United States Patent
Altmann et al.

(12) 
(10) Patent No.: US 6,225,446 B1
(45) Date of Patent: *May 1, 2001

(54) MUTATIONAL VARIANTS OF MAMMALIAN PROTEINS

(75) Inventors: Scott W. Altmann, Kenilworth, NJ (US); Fernando L. Rock, Foster City, CA (US); J. Fernando Bazan, Menlo Park, CA (US); Robert A. Kastelein, Redwood City, CA (US)

(73) Assignee: Schering Corporation, Kenilworth, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/759,628

(22) Filed: Dec. 5, 1996

Related U.S. Application Data

(60) Provisional application No. 60/008,574, filed on Dec. 6, 1995.

(51) Int. Cl.$^7$ .................................................. C07K 14/52
(52) U.S. Cl. ..................... 530/351; 530/350; 530/324; 530/399; 424/85.2; 514/2
(58) Field of Search ............................... 435/69.1, 69.52, 435/172.1, 172.3; 514/2; 530/350, 351, 324, 399; 424/85.2

(56) References Cited

FOREIGN PATENT DOCUMENTS

| | | |
|---|---|---|
| 0 743 321 A2 | 5/1996 | (EP) . |
| 0 744 408 A2 | 5/1996 | (EP) . |
| 0 725 078 A1 | 8/1996 | (EP) . |
| 0 725 079 A1 | 8/1996 | (EP) . |
| WO 96/05309 | 2/1996 | (WO) . |
| WO 96/24670 | 8/1996 | (WO) . |

OTHER PUBLICATIONS

Takashi Murakami, et al., *Biochem. Biophys. Res. Comm.*, 209(3):944–952, Apr. 26, 1995. "Cloning of Rat Obese cDNA and Its Expression in Obese Rats".

Naoko Arai, et al., Gen Bank Accession No. M23442, pp. 1–4, Jan. 1995.

Marcia Barinaga, *Science*, 269:475–476, Jul. 28, 1995, "'Obese' Protein Slims Mice".

J. Fernando Bazan, *Immunol. Today*, 11:350–354, 1990, "Haemopoietic receptors and helical cytokines".

J. Fernando Bazan, *Science*, 257:410–413, Jul. 17, 1992. "Unraveling the Structure of IL–2".

George A. Bray, et al., *Physiol. Rev.*, 59:719–809, Jul. 1979 "Hypothalamic and Genetic Obesity in Experimental Animals: an Autonomic and Endocrine Hypothesis".

L. Arthur Campfield, et al., *Science*, 269:546–548, Jul. 28, 1995 "Recombinanat Mouse OB Protein: Evidence for a Peripheral Signal Linking Adiposity and Central Neural Networks".

Streamson C. Chua Jr., et al., *Science*, 271:994–996, Feb. 16, 1996 "Phenotypes of Mouse diabetes and Rat fatty Due to Mutations in the OB (Leptin) Receptor".

Jeffrey L. Halaas, et al., *Science*, 269:543–546, Jul. 28, 1995. "Weight–Reducing Effects of the Plasma Protein Encoded by the obese Gene".

N.J. Holbrook, et al., Gen Bank Accession No. K02056, pp. 1–3, May 1996.

F. Lee, et al., Gen Bank Accession No. M11220, p. 1, Nov. 1994.

Y. Ogawa et al., Gen Bank Accession No. D45862, p. 1, Nov. 1996.

Mary Ann Pelleymounter, et al., *Science*, 269:540–543, Jul. 28, 1995 "Effects of the obese Gene Product on Body Weight Regulation in ob/ob Mice".

Denise Rozwarski, et al., *Structure*, 2:159–173, Mar. 15, 1994 "Structural comparisons among the short–chain helical cytokines".

P.H. Seeburg, Gen Bank Accession No. M13438, pp. 1–3, Apr. 1996.

Stephen R. Sprang, et al., *Curr. Opin. Struct. Biol.* 3:815–827, 1993 "Cytokine structural taxonomy and mechanisms of receptor engagement".

T. Tanabe, et al., Gen Bank Accession No. J03478, pp. 1–2, Aug. 1995.

G.G. Wong, et al., Gen Bank Accession No. M37435, pp. 1–2, Nov. 1994.

Y. Zhang, et al., Gen Bank Accession No. U18812, pp. 1–2, Mar. 1995.

Y. Zhang et al., Gen Bank Accession No. U18915, p. 1, Jan. 1995.

Yiying Zhang, et al., *Nature* 372:425–432, Dec. 1, 1994 "Positional cloning of the mouse obese gene and its human homologue".

Sandra M. Zurawski, et al., *J. Immunol.* 137:3354–3360, Nov. 15, 1986 "Alternations in the Amino–Terminal Third of Mouse Interleukin 2: Effects on Biological Activity and Immunoreactivity".

(List continued on next page.)

Primary Examiner—Laurie Scheiner
(74) Attorney, Agent, or Firm—Edwin P. Ching; Hugh Wang

(57) ABSTRACT

Muteins, which are mutational variants of mammalian proteins. Particular positions of natural proteins are identified as critical in providing various different activities. Specific embodiments demonstrate properties of variations at these positions.

17 Claims, 4 Drawing Sheets

OTHER PUBLICATIONS

Sandra M. Zurawski, et al., *EMBO J.* 7:1061–1069, 1988 "Identification for three critical regions within mouse interleukin 2 by fine structural deletion analysis".

Sandra M. Zurawaki, et al., *EMBO J.* 8:2583–2590, 1989, "Mouse interleukin–2 structure–function studies: substitutions in the first α–helix can specifically inactivate p70 receptor binding and mutations in the fifth α–helix can specifically inactivate p55 receptor binding".

Sandra M. Zurawski, et al., *EMBO J.* 12:2663–2670, 1993 "Receptors for interleukin–13 and interleukin–4 are complex and share a novel component that functions in signal transduction".

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 167 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
            85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
            115                 120                 125

Asp Ser Leu Gly Gly Val Leu Glu Ala Ser Gly Tyr Ser Thr Glu Val
            130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

(2) INFORMATION FOR SEQ ID NO:2:

(i) SEQUENCE CHARACTERISTICS:
        (A) LENGTH: 167 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Cys Trp Arg Pro Leu Cys Arg Phe Leu Trp Leu Trp Ser Tyr Leu
1               5                   10                  15

Ser Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
            35                  40                  45

Gln Ser Val Ser Ala Lys Gln Arg Val Thr Gly Leu Asp Phe Ile Pro
50                  55                  60

Gly Leu His Pro Ile Leu Ser Leu Ser Lys Met Asp Gln Thr Leu Ala
65                  70                  75                  80

Val Tyr Gln Gln Val Leu Thr Ser Leu Pro Ser Gln Asn Val Leu Gln
            85                  90                  95

Ile Ala Asn Asp Leu Glu Asn Leu Arg Asp Leu Leu His Leu Leu Ala
            100                 105                 110

Phe Ser Lys Ser Cys Ser Leu Pro Gln Thr Ser Gly Leu Gln Lys Pro
            115                 120                 125

```
Glu Ser Leu Asp Gly Val Leu Glu Ala Ser Leu Tyr Ser Thr Glu Val
        130                 135                 140

Val Ala Leu Ser Arg Leu Gln Gly Ser Leu Gln Asp Ile Leu Gln Gln
145                 150                 155                 160

Leu Asp Val Ser Pro Glu Cys
                165

(2) INFORMATION FOR SEQ ID NO:3:

(i) SEQUENCE CHARACTERISTICS:
        (A) LENGTH: 167 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Cys Trp Arg Pro Leu Cys Arg Phe Leu Trp Leu Trp Ser Tyr Leu
1               5                   10                  15

Ser Tyr Val Gln Ala Val Pro Ile His Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ala Arg Gln Arg Val Thr Gly Leu Asp Phe Ile Pro
    50                  55                  60

Gly Leu His Pro Ile Leu Ser Leu Ser Lys Met Asp Gln Thr Leu Ala
65                  70                  75                  80

Val Tyr Gln Gln Ile Leu Thr Ser Leu Pro Ser Gln Asn Val Leu Gln
                85                  90                  95

Ile Ala His Asp Leu Glu Asn Leu Arg Asp Leu Leu His Leu Leu Ala
            100                 105                 110

Phe Ser Lys Ser Cys Ser Leu Pro Gln Thr Arg Gly Leu Gln Lys Pro
        115                 120                 125

Glu Ser Leu Asp Gly Val Leu Glu Ala Ser Leu Tyr Ser Thr Glu Val
        130                 135                 140

Val Ala Leu Ser Arg Leu Gln Gly Ser Leu Gln Asp Ile Leu Gln Gln
145                 150                 155                 160

Leu Asp Leu Ser Pro Glu Cys
                165

(2) INFORMATION FOR SEQ ID NO:4:

(i) SEQUENCE CHARACTERISTICS:
        (A) LENGTH: 440 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Leu Pro Leu Leu Pro Leu Leu Trp Ala Gly Ala Leu Ala Gln
1               5                   10                  15

Glu Arg Arg Phe Gln Leu Glu Gly Pro Glu Ser Leu Thr Val Gln Glu
                20                  25                  30

Gly Leu Cys Val Leu Val Pro Cys Arg Leu Pro Thr Thr Leu Pro Ala
            35                  40                  45

Ser Tyr Tyr Gly Tyr Gly Tyr Trp Phe Leu Glu Gly Ala Asp Val Pro
```

-continued

```
            50                  55                  60
Val Ala Thr Asn Asp Pro Asp Glu Val Gln Glu Thr Arg Gly
 65                  70                  75                  80

Arg Phe His Leu Leu Trp Asp Pro Arg Arg Lys Asn Cys Ser Leu Ser
                     85                  90                  95

Ile Arg Asp Ala Arg Arg Asp Asn Ala Ala Tyr Phe Phe Arg Leu
                100                 105                 110

Lys Ser Lys Trp Met Lys Tyr Gly Tyr Thr Ser Ser Lys Ile Tyr Val
                115                 120                 125

Arg Val Met Ala Leu Thr His Arg Pro Asn Ile Ser Ile Pro Gly Pro
                130                 135                 140

Gly Val Trp Pro Ser Ser Asn Leu Thr Cys Ser Val Pro Trp Val Cys
145                 150                 155                 160

Glu Gln Gly Thr Pro Pro Ile Phe Ser Trp Met Ser Ala Ala Pro His
                    165                 170                 175

Leu Leu Gly Pro Arg Thr Thr Gln Ser Ser Val Leu Thr Ile Thr Pro
                180                 185                 190

Ala Gln Asp His Ser Thr Asn Leu Thr Cys Gln Val Thr Phe Pro Gly
                195                 200                 205

Ala Gly Val Thr Met Glu Arg Thr Ile Gln Leu Asn Val Ser Tyr Ala
                210                 215                 220

Pro Gln Lys Val Ala Ile Ser Ile Phe Gln Gly Asn Ser Ala Ala Phe
225                 230                 235                 240

Lys Ile Leu Gln Asn Thr Ser Ser Leu Pro Val Leu Glu Gly Gln Ala
                    245                 250                 255

Leu Arg Leu Leu Cys Asp Ala Asp Gly Asn Pro Pro Ala His Leu Ser
                260                 265                 270

Trp Phe Gln Ala Ser Pro Pro Xaa Asn Ala Thr Pro Ile Ser Asn Thr
                275                 280                 285

Gly Val Leu Glu Leu Pro Gln Val Gly Ser Ala Glu Glu Gly Asp Phe
290                 295                 300

Thr Cys Arg Ala Gln His Pro Leu Gly Ser Leu Gln Ile Ser Leu Ser
305                 310                 315                 320

Leu Phe Val His Trp Lys Pro Glu Gly Arg Ala Gly Gly Val Leu Gly
                    325                 330                 335

Ala Val Trp Gly Ala Ser Ile Thr Thr Leu Val Phe Leu Cys Val Cys
                340                 345                 350

Phe Ile Phe Arg Val Lys Thr Arg Arg Lys Lys Gln Pro Ser Gln Cys
                355                 360                 365

Lys Xaa Thr Asp Asp Val Asn Pro Val Met Val Ser Gly Ser Arg Gly
                370                 375                 380

His Gln His Gln Phe Gln Thr Gly Ile Val Ser Asp His Pro Ala Glu
385                 390                 395                 400

Ala Gly Pro Ile Ser Glu Asp Glu Gln Glu Leu His Tyr Ala Val Leu
                    405                 410                 415

His Phe His Lys Val Gln Pro Gln Glu Pro Lys Val Thr Asp Thr Glu
                420                 425                 430

Tyr Ser Glu Ile Lys Ile His Lys
                435                 440
```

(2) INFORMATION FOR SEQ ID NO:5:

(i) SEQUENCE CHARACTERISTICS:
        (A) LENGTH: 421 amino acids (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Pro Leu Leu Leu Pro Leu Leu Trp Gly Gly Ser Leu Gln Glu
1               5                   10                  15

Lys Pro Val Tyr Glu Leu Gln Val Gln Lys Ser Val Thr Val Gln Glu
                20                  25                  30

Gly Leu Cys Val Leu Val Pro Cys Ser Phe Ser Tyr Pro Trp Arg Ser
                35                  40                  45

Trp Tyr Ser Ser Pro Pro Leu Tyr Val Tyr Trp Phe Arg Asp Gly Glu
50                  55                      60

Ile Pro Tyr Tyr Ala Glu Val Val Ala Thr Asn Asn Pro Asp Arg Arg
65                  70                  75                  80

Val Lys Pro Glu Thr Gln Gly Arg Phe Arg Leu Leu Gly Asp Val Gln
                85                  90                  95

Lys Lys Asn Cys Ser Leu Ser Ile Gly Asp Ala Arg Met Glu Asp Thr
                100                 105                 110

Gly Ser Tyr Phe Phe Arg Val Glu Arg Gly Arg Asp Val Lys Tyr Ser
                115                 120                 125

Tyr Gln Gln Asn Lys Leu Asn Leu Glu Val Thr Ala Leu Ile Glu Lys
130                 135                 140

Pro Asp Ile His Leu Ser Gly Pro Leu Glu Ser Gly Leu Trp Arg Pro
145                 150                 155                 160

Thr Arg Leu Ser Cys Ser Leu Pro Gly Ser Cys Val Ala Gly Pro Pro
                165                 170                 175

Leu Thr Phe Ser Trp Thr Gly Asn Ala Xaa Ser Ala Pro Trp Thr Pro
                180                 185                 190

Arg Pro Xaa Ala Pro Arg Glu Leu Thr Leu Thr Pro Arg Pro Glu Asp
                195                 200                 205

His Gly Thr Asn Leu Thr Cys Gln Met Lys Arg Gln Gly Ala Gln Val
                210                 215                 220

Thr Thr Glu Xaa Thr Val Gln Leu Asn Val Ser Tyr Ala Pro Gln Thr
225                 230                 235                 240

Ile Thr Ile Phe Arg Asn Gly Ile Ala Leu Glu Ile Leu Gln Asn Thr
                245                 250                 255

Ser Tyr Leu Pro Val Leu Glu Gly Gln Ala Leu Arg Leu Leu Cys Asp
                260                 265                 270

Ala Pro Ser Asn Pro Pro Ala His Leu Ser Trp Phe Gln Gly Ser Pro
                275                 280                 285

Ala Leu Asn Ala Thr Pro Ile Ser Asn Thr Gly Ile Leu Glu Leu Arg
                290                 295                 300

Arg Val Arg Ser Ala Glu Glu Gly Gly Phe Thr Cys Arg Ala Gln His
305                 310                 315                 320

Pro Leu Gly Phe Leu Gln Ile Phe Leu Asn Leu Ser Val Tyr Ser Leu
                325                 330                 335

Pro Gln Leu Leu Gly Pro Ser Cys Ser Trp Glu Ala Glu Gly Leu His
                340                 345                 350

Cys Arg Cys Ser Phe Arg Ala Arg Pro Ala Pro Ser Leu Cys Trp Arg
                355                 360                 365

Leu Asp Glu Lys Pro Leu Glu Gly Asn Ser Ser Gln Gly Ser Phe Lys
370                 375                 380

```
Val Asn Ser Ser Ser Ala Xaa Pro Gly Gln Gln Leu Pro Asp Pro Pro
385                 390                 395                 400

Arg Gly Ala Gln Leu Arg Thr Ser Lys Ser Ala Ala Arg Pro Gly Thr
            405                 410                 415

Ser Met Gly Pro Glu
            420
```

Figure 1B:
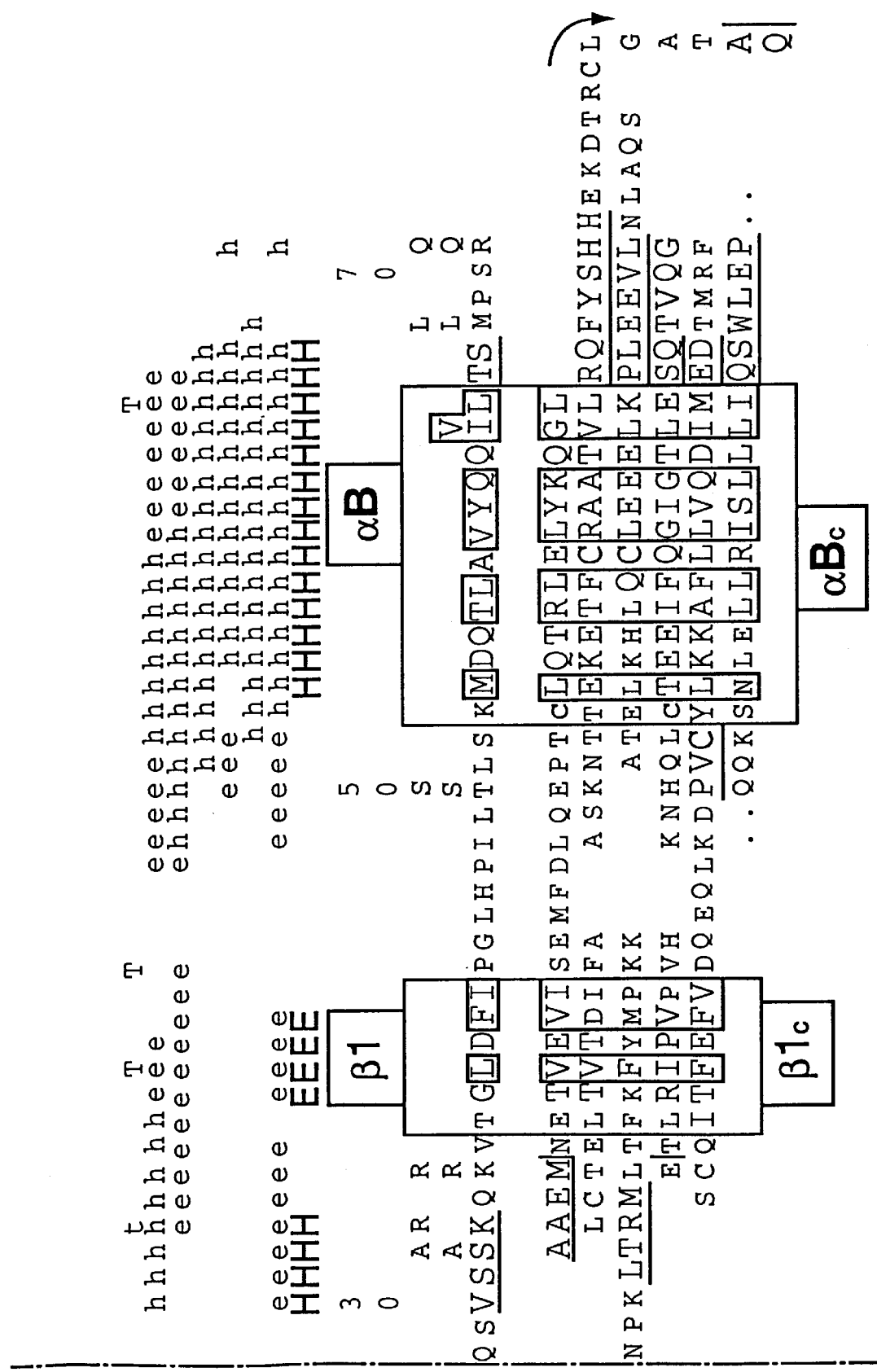
Figure 1C:
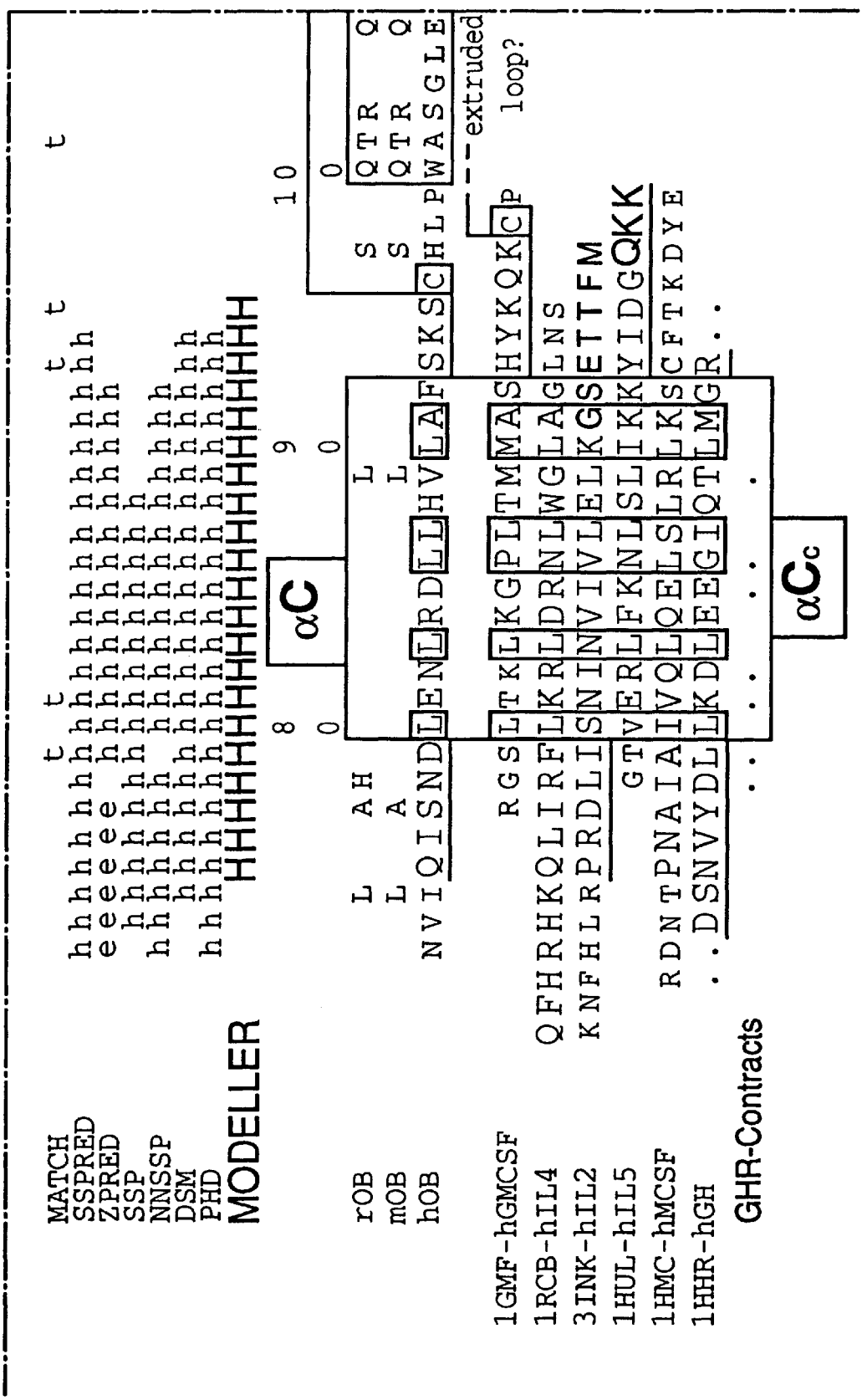
Figure 1D:
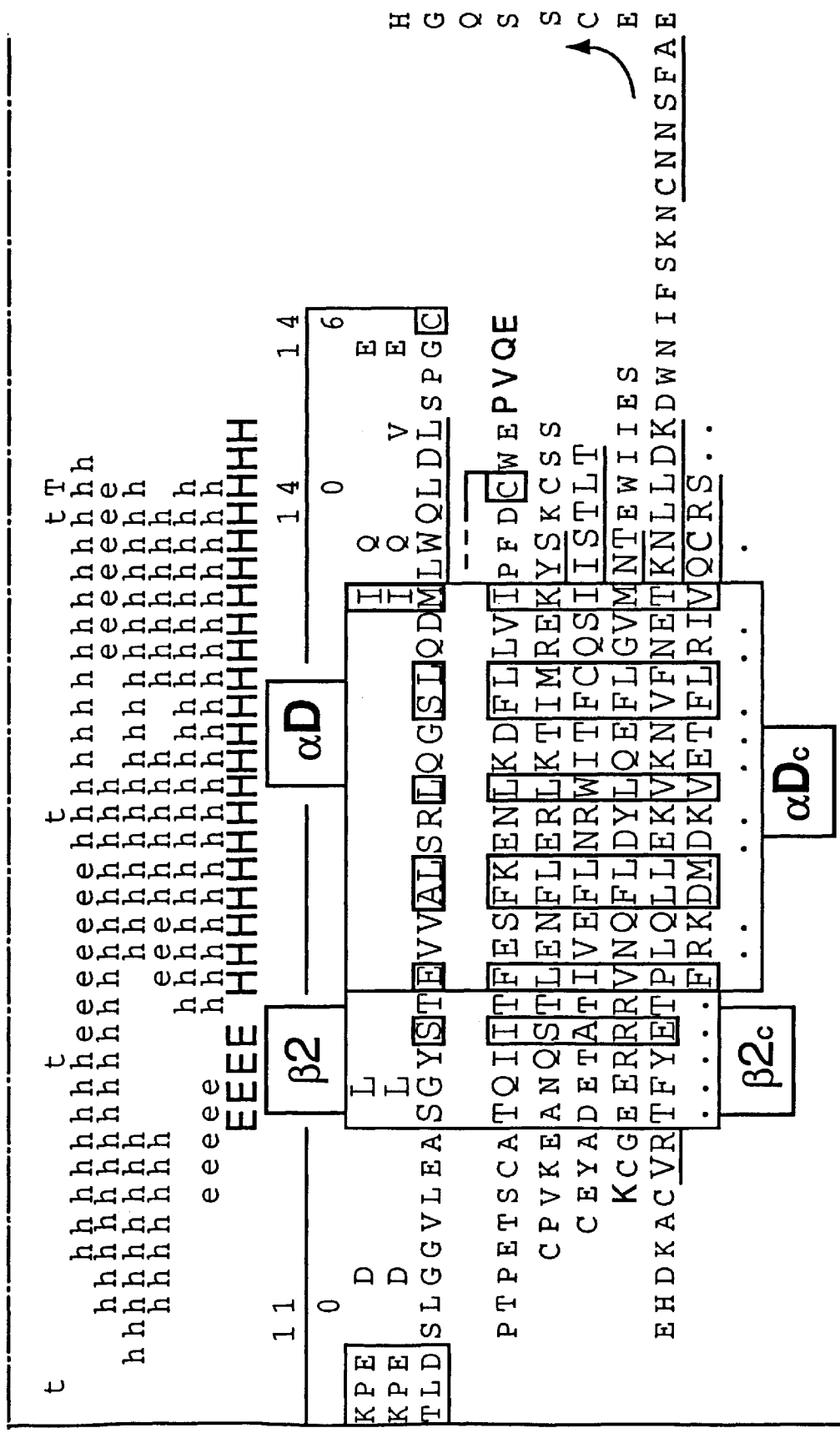

(2) INFORMATION FOR SEQ ID NO:6:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Peptide
        (B) LOCATION: 18..144
        (D) OTHER INFORMATION: /note= "peptide of Figure 1"

(xi) SEQUENCE DESCRIPTION: SEQ ID NO:6:

```
Met Trp Leu Gln Ser Leu Leu Leu Gly Thr Val Ala Cys Ser Ile
1               5                   10                  15

Ser Ala Pro Ala Arg Ser Pro Ser Thr Gln Pro Trp Glu His
                20              25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Thr Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
            130                 135                 140
```

(2) INFORMATION FOR SEQ ID NO:7:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Peptide
        (B) LOCATION: 25..153
        (D) OTHER INFORMATION: /note= "Peptide of Figure 1"

(xi) SEQUENCE DESCRIPTION: SEQ ID NO:7:

```
Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
                20                  25                  30
```

```
Glu Ile Ile Lys Thr Leu Asn Ser Leu Thr Glu Gln Lys Thr Leu Cys
            35                  40                  45

Thr Glu Leu Thr Val Thr Asp Ile Phe Ala Ala Ser Lys Asn Thr Thr
 50                  55                  60

Glu Lys Glu Thr Phe Cys Arg Ala Ala Thr Val Leu Arg Gln Phe Tyr
 65                  70                  75                  80

Ser His His Glu Lys Asp Thr Arg Cys Leu Gly Ala Thr Ala Gln Gln
                 85                  90                  95

Phe His Arg His Lys Gln Leu Ile Arg Phe Leu Lys Arg Leu Asp Arg
                100                 105                 110

Asn Leu Trp Gly Leu Ala Gly Leu Asn Ser Cys Pro Val Lys Glu Ala
            115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150
```

(2) INFORMATION FOR SEQ ID NO:8:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Peptide
        (B) LOCATION: 21..153
        (D) OTHER INFORMATION: /note= "Peptide of Figure 1"

(xi) SEQUENCE DESCRIPTION: SEQ ID NO:8:

```
Met Tyr Arg Met Gln Leu Leu Ser Cys Ile Ala Leu Ser Leu Ala Leu
 1               5                  10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
 50                  55                  60

Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                 85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

(2) INFORMATION FOR SEQ ID NO:9:

(i) SEQUENCE CHARACTERISTICS:
        (A) LENGTH: 134 amino acids
        (B) TYPE: amino acid
        (C) STRANDEDNESS: single

```
            (D) TOPOLOGY: linear (ii) MOLECULE TYPE: protein (ix) FEATURE:
            (A) NAME/KEY: Peptide
            (B) LOCATION: 20..134
            (D) OTHER INFORMATION: /note= "Peptide of Figure 1"

(xi) SEQUENCE DESCRIPTION: SEQ ID NO:9:

Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
                20                  25                  30

Thr Leu Ala Leu Leu Ser Thr His Arg Thr Leu Leu Ile Ala Asn Glu
            35                  40                  45

Thr Leu Arg Ile Pro Val Pro Val His Lys Asn His Gln Leu Cys Thr
        50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Lys Cys Gly Glu Glu Arg Arg Arg Val
                100                 105                 110

Asn Gln Phe Leu Asp Tyr Leu Gln Glu Phe Leu Gly Val Met Asn Thr
            115                 120                 125

Glu Trp Ile Ile Glu Ser
            130

(2) INFORMATION FOR SEQ ID NO:10:

(i) SEQUENCE CHARACTERISTICS:
            (A) LENGTH: 184 amino acids
            (B) TYPE: amino acid
            (C) STRANDEDNESS: single
            (D) TOPOLOGY: linear (ii) MOLECULE TYPE: protein (ix) FEATURE:
            (A) NAME/KEY: Peptide
            (B) LOCATION: 33..184
            (D) OTHER INFORMATION: /note= "Peptide of Figure 1"

(xi) SEQUENCE DESCRIPTION: SEQ ID NO:10:

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
                20                  25                  30

Glu Glu Val Ser Glu Tyr Cys Ser His Met Ile Gly Ser Gly His Leu
            35                  40                  45

Gln Ser Leu Gln Arg Leu Ile Asp Ser Gln Met Glu Thr Ser Cys Gln
        50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
                100                 105                 110

Gln Glu Leu Ser Leu Arg Leu Lys Ser Cys Phe Thr Lys Asp Tyr Glu
            115                 120                 125
```

```
Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Glu Cys Ser Ser Gln Gly His
            180
```

(2) INFORMATION FOR SEQ ID NO:11:

(i) SEQUENCE CHARACTERISTICS:
        (A) LENGTH: 217 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Peptide
        (B) LOCATION: 32..53

(ix) FEATURE:
        (A) NAME/KEY: Peptide
        (B) LOCATION: 94..115

(ix) FEATURE:
        (A) NAME/KEY: Peptide
        (B) LOCATION: 133..153

(ix) FEATURE:
        (A) NAME/KEY: Peptide
        (B) LOCATION: 192..210
        (D) OTHER INFORMATION: /note= "The peptides above are
            depicted in Figure 1"

(xi) SEQUENCE DESCRIPTION: SEQ ID NO:11:

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
    115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190
```

```
Arg Lys Asp Met Asp Lys Val Glu Thr Phe Leu Arg Ile Val Gln Cys
        195                 200                 205
Arg Ser Val Glu Gly Ser Cys Gly Phe
    210                 215
```

MUTATIONAL VARIANTS OF MAMMALIAN PROTEINS

This application claims priority to U.S. Provisional Patent application Ser. No. 60/008,574 by Altmann, et al. filed Dec. 6, 1995, which is incorporated herein by reference.

FIELD OF THE INVENTION

The present invention relates to compositions which include variants of human Ob, a protein exhibiting cytokine—like structure, which functions in regulating metabolism and weight. In particular, it provides agonists and/or antagonists of said protein.

BACKGROUND OF THE INVENTION

Recent studies have identified a protein product, designated Ob, which when injected into a mouse causes that animal to lose weight. See, e.g., Barinaga (1995) *Science* 269:475–476; Zhang, et al. (1994) *Nature* 372:425–432; Pelleymounter, et al. (1995) *Science* 269:540–543; Halaas, et al. (1995) *Science* 269:543–546; and Campfield, et al. (1995) *Science* 269:546–548. Mice deficient in active Ob gene product are grossly obese, but injection of the Ob protein causes the mice to curb their eating and shed fat.

Physiologically, it appears that the Ob protein has two activities, it decreases appetite and increases energy use, leading to metabolic deficit and loss of weight.

In the United States, up to one third of all Americans are overweight. Obesity is the cause of a myriad of serious health problems, including, e.g., sleep apnea, adult-onset diabetes, and heart disease. See, e.g., The Merck Manual. The availability of agonists and antagonists will be used to modulate these processes. The present invention provides these, as well as other proteins, useful, e.g., in determining the structure and mechanisms of weight and appetite regulation.

SUMMARY OF THE INVENTION

The present invention provides molecules which can serve as an agonist or antagonist for the Ob proteins. These agonists and antagonists will be useful in regulating weight and appetite regulation, and may be important in other hematopoietic or immunological function. In certain circumstances, these molecules will also have in vitro or in vivo therapeutic effects.

The present invention is based, in part, upon the recognition by structural analysis of the Ob sequence that it shares structural homology with a subclass of proteins known as cytokines. Cytokines are molecules which mediate differentiation or other signals, typically between he circulating component of the mammalian circulatory system. Ob belongs to the subgroup of hematopoietic cytokines, which includes IL-2, IL-4, IL-5, GM-CSF, and growth hormone.

In particular, this insight leads to recognition of which specific amino acid residues of a cytokine—like protein are important in receptor binding. It embraces various mutein agonists and antagonists of natural ligands, e.g., specific mutations (muteins) of the natural sequences, fusion proteins, and chemical mimetics. It is also directed to DNAs encoding such variant proteins. Various uses of these different protein or nucleic acid compositions are also provided.

The present invention provides a mutein of a mammalian Ob which comprises a variation in sequence at a position in a solvent exposed residue in helix A; in a solvent exposed residue in helix C; in extruded loop from 100 to 108; or in a solvent exposed residue in helix D. In preferred embodiments, the position is in helix A; the mammalian Ob is mouse Ob, rat Ob, or human Ob; the Ob has a sequence of SEQ ID NO: 1, 2, or 3; the variation is a non-conservative substitution; the substitution is at a position corresponding to D8, D9, K11, T12, K15, T16, V18, T19, I21, N22, N78, H78, D79, E81, N82, R84, D85, L86, V89, V123, V124, S127, R128, Q130, G131, S132, Q134, D135, or W138; the substitution is at a position corresponding to D8, D9, K11, T12, K15, T16, T19, E81, N82, R84, D85, R128, Q130, Q134, or D135; the substitution is selected from D8K, D9K, K11E, T12E, K15E, T16E, T19E, E81K, N82D, R84E, D85K, R128E, Q130K, Q134K, or D135K; and/or the variation is in the extruded loop at a position between 100 and 108, including deletion of amino acid residues 121–129 in SEQ ID NO: 1, 2, or 3.

In other embodiments, the mutein exhibits at least about a 30% decrease in biological activity; exhibits less than about 80% maximal agonist activity; or exhibits at a 100-fold excess antagonist activity of said mammalian Ob by at least about 50%; will have a sequence variation which disrupts helical structure of helix A, C, or D; or will competitively compete with mammalian OB.

The invention also embraces a pharmaceutical composition comprising the mutein a pharmaceutically acceptable carrier or excipient. It also embraces a nucleic acid encoding these muteins.

In other embodiments, the invention provides a method of antagonizing the biological activity of a mammalian Ob on a cell comprising contacting the cell with a described mutein. Preferably the biological activity is receptor binding and the method includes decreasing appetite or increasing metabolic rate in a mammal.

DETAILED DESCRIPTION OF THE PREFERRED EMBODIMENTS

Figure 1A:
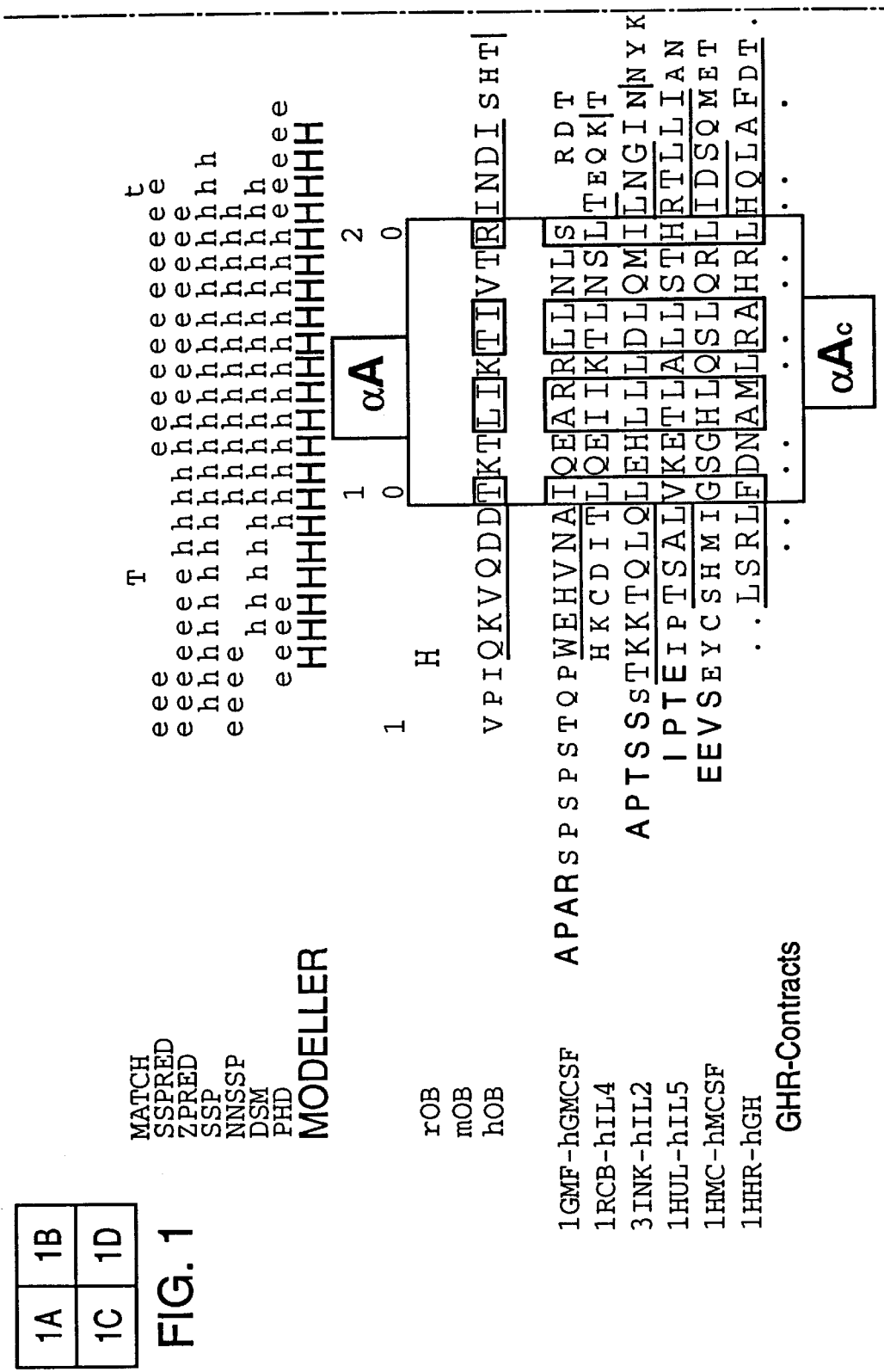
FIGS. 1A, 1B, 1C and 1D show alignment of various members of the hematopoietic cytokine group.

OUTLINE
  I. General
  II. Agonists; antagonists
  III. Physical Variants
    A. fragments
    B. post-translational variants
      1. glycosylation
      2. others
    C. species variants
  IV. Nucleic Acids
    A. mutated natural isolates; methods
    B. synthetic genes
    C. methods to isolate
  V. Antibodies
    A. polyclonal
    B. monoclonal
    C. fragments, binding compositions
  VI. Making Agonists and Antagonists
    A. recombinant methods
    B. synthetic methods
    C. natural purification
  VII. Uses
    A. diagnostic
    B. therapeutic
  VIII. Kits
    A. nucleic acid reagents
    B. protein reagents C. antibody reagents I. General The present invention is based, in part, upon the recognition by structural analysis of the Ob sequence that it shares numbers of each cytokine, and references providing gene and/or cytokine amino acid sequence. Many receptor sequences are also available from GenBank. See also Howard, et al. (1993) in Paul (ed.) (1993) *Fundamental Immunology* (3d ed.) Raven Press, N.Y.

TABLE 1

Mammalian Ob proteins sequences (human SEQ ID NO: 1, mouse SEQ ID NO: 2, rat SEQ ID NO: 3).

```
Mob  MCWRPLCRFLWLWSYLSYVQA VPIQKVQDDT KTLIKTIVTR INDISHTQSV
Rob  MCWRPLCRFLWLWSYLSYVQA VPIHKVQDDT KTLIKTIVTR INDISHTQSV
Hob  MHWGTLCGFLWLWPYLFYVQA VPIQKVQDDT KTLIKTIVTR INDISHTQSV
     * *  ** ***** ** **** ***.****** ********** **********

Mob  SAKQRVTGLD FIPGLHPILS LSKMDQTLAV YQQVLTSLPS QNVLQIANDL
Rob  SARQRVTGLD FIPGLHPILS LSKMDQTLAV YQQTLTSLPS QNVLQIAHDL
Hob  SSKQKVTGLD FIPGLHPILT LSKMDQTLAV YQQILTSMPS RNVIQISNDL
     *..*.***** *********. ********** ***.***.** .**.**..**

Mob  ENLRDLLHLL AFSKSCSLPQ TSGLQKPESL DGVLEASLYS TEVVALSRLQ
Rob  ENLRDLLHLL AFSKSCSLPQ TRGLQKPESL DGVLEASLYS TEVVALSRLQ
Hob  ENLRDLLHVL AFSKSCHLPW ASGLETLDSL GGVLEASGYS TEVVALSRLQ
     ********.* ****** **  . **.  .** ****** ** **********

Mob  GSLQDILQQL DVSPEC
Rob  GSLQDILQQL DLSPEC
Hob  GSLQDMLWQL DLSPGC
     *****.* ** *.** *
``` first 21 residues appear to be signal sequence, mature protein amino terminus begins at residue 22 (VPI...), residue numbering used herein is relative to that; * denotes matching residues among all three sequences. Mouse Ob sequence is GenBank Accession Number U18812; rat is D45862; human is U128915.

structural motifs and striking similarity to proteins known as hematopoietic cytokines. This is emphasized, e.g., by the similarity in CD spectrum of Ob with other hematopoietic cytokines. Cytokines are molecules which mediate differentiation or other signals, typically between he circulating cell components of the mammalian circulatory system.

These cells are of many types, including red and white blood cells of the erythroid or the myeloid cell lineages. See, e.g., Rapaport (1987) *Introduction to Hematology* (2d ed.) Lippincott, Philadelphia, Pa; Jandl (1987) *Blood: Textbook of Hematology*, Little, Brown and Co., Boston, Mass.; and Paul (ed.) (1993) *Fundamental Immunology* (3d ed.), Raven Press, N.Y. Myeloid cell production occurs through the differentiation and later commitment of myeloid progenitor cell lineages.

In addition, functional interaction of the various cell types involved in immune responses often involve transfer of signals via soluble messenger molecules. Cytokines function through receptors, many of which have been characterized. See, e.g., Aggarwal and Gutterman (eds.) (1991) *Human Cytokines: Handbook for Basic and Clinical Research*, Blackwell, Oxford.

It is presumed that the Ob protein operates through a similar biological signal mechanism, with the described effects on organismic physiology. Moreover, the similarity to cytokines may suggest additional effects on hematopoietic or immunological development or function.

The present invention provides sequence variants, also referred to as mutant proteins (muteins), of the Ob proteins, e.g., muteins, which serve as agonists and/or antagonists of the cytokines. The natural ligands are capable of mediating various biochemical responses which should lead to biological or physiological responses in target cells, e.g., as described above.

Physically, relevant cytokines have been described, as shown in Table 1. The table provides the GenBank accession With a selected cell line, a dose-response curve of the appropriate cytokine is performed. This gives a plateau, or maximal stimulation at saturating or excess amounts of cytokine. Typically, the cytokine will show a useful dose-response in the range of $10^{-7}$ to $10^{-13}$ M cytokine. The half maximal response typically will fall in the range of $10^{-9}$ to $10^{-12}$ M.

A mutein candidate agonist is tested, preferably with a sequence substitution as described, by measuring biological activity upon administration. In one assay, a dose response curve of the Ob is titrated in the absence or presence of the candidate mutein at a fixed concentration. Typically the candidate mutein concentration is fixed, preferably within the range of equimolar to the half-maximum of the target cytokine, or at a 10-, 100-, or 1000-fold excess of candidate mutein over that half-maximum amount. Typically, the dose response curve of the cytokine will shift. The shift will normally be at least one log unit, often two to four log units.

To test partial agonist activity of the candidate mutein, a dose-response curve of the mutein is performed. Assays for biological activity in animals are known. Typically, the maximal stipulatory activity of the mutein will be near that of the natural cytokine, but partial agonists will show a suboptimal stimulation at saturation, e.g., the maximal activity will plateau at a lesser amount. This amount will often be less than about 90%, preferably less than about 75%, more preferably less than about 50%, and in most preferred embodiments, even less than about 25%. Agonists with an even lesser maximum will still be useful, and often provide the most promising candidates for establishing chemical antagonist properties. Super-activating agonists will have greater activities. These activity amounts will often be greater than 110%, typically greater than 120%, preferably greater than 130%, and in most preferred embodiments, greater than 150%.

Muteins are made typically by site specific mutagenesis of natural cytokine at defined positions. The sequences of the Ob proteins and cytokines are referred to in Table 1, GenBank, and the references cited therein. Initially, single and low multiplicity mutagenesis will be constructed, with more complex combinations also available. The tertiary structural features of cytokines have been described, e.g., in Bazan (1991) *Cell* 66:9–10; Bazan (1990) *Immunology Today* 11:350–354; Bazan (1992) *Science* 257:410–413; Rozwarski, et al. (1994) *Structure* 2:159–173; and Sprang and Bazan (1993) *Current Opinion in Structural Biology* 3:815–827. These references define common structural features of the cytokines, e.g., the helices A, B, C, and D therein, including sequence alignments and corresponding positions. See also Zurawski, et al. (1993) *EMBO J.* 12:2663–2670; and the programs MATCH, SSPRED, ZIPPED, SSP, NNSSP, DSM, PHD, and MODELLER. The specific positions of critical substitutions typically are conserved across different cytokines in various patterns, and because the helical turn involves 3.5 residues per turn, 3 or 4 residues and 7 residues in either direction will be positioned adjacent on the surface of a cytokine. Helix A of the mammalian Ob correspond to positions 4–24; helix B to positions 54–67; helix C to positions 75–92; and helix D to positions 117–142. The region of Ob protein predicted to interact with its receptor would be the A (and secondarily C) and D helices. Structurally, positions 10; 13, 14; 16, 17; and 20 in helix A; positions 80; 83; 86, 87; and 90, 91 in helix C; and positions 120; 122; 125, 126; 129; 132, 133; and 136 in helix D are each predicted to be in a helical structure whose surface is away from the receptor contact site and less critical in binding protein, e.g., receptor, interaction. Consequently, positions which would be on the helical surface contacting its receptors would be expected to have a more dramatic effect on interaction, e.g., binding or signaling. Particularly important residues include, e.g., K11, T12, K15, T16, or T19 in helix A; R128, Q130, Q134, or D135 in helix D; E81, N82, R84, or D85 in helix C. Significant changes in the nature of solvent exposed residues, e.g., charge reversal or significant size or hydrophobicity change, would be more likely to significantly affect physiological result. Also, significant disruption of the secondary structure, e.g., helical structure, would be also expected to abolish receptor interaction. Conservative substitutions generally would be expected to exhibit similar biological activity.

In addition, the Ob proteins exhibit an "extruded loop" structure, e.g., residues 100–108, which is not found in the related cytokines. Deletion of this segment results in a protein which lacks physiological activity, e.g., including appetite suppression and weight loss, but still retains binding capabilities to its receptor.

II. Agonists; antagonists

The process of inhibition or prevention of agonist-induced responses is termed antagonism, and chemical entities with such properties are antagonists. See, e.g., Kenakin (1987) *Pharmacological Analysis of Drug-Receptor Interaction* Raven Press, N.Y.

Various classes of antagonists include chemical or neutralization antagonists, competitive antagonists, and non-competitive antagonists. The chemical or neutralization antagonists typically interact with the agonist and prevent activation of the receptor and subsequent response, e.g., antibody antagonists which bind to the agonist and block signaling thereby. Variant proteins are purified and subjected to physical analysis, e.g., CD analysis, to determine whether the protein has a native-like conformation. Its binding behavior is tested, e.g., on cells expressing natural or recombinant receptor. The effects of the Ob variants may also be tested in the mice, e.g., the ob-/ob- animals.

The competitive antagonists typically are molecules which bind to the same recognition site on the receptor and block agonist binding. Noncompetitive antagonists bind to a site on the receptor distinct from the agonist binding site, and block signal transduction.

Measurement of antagonist activity and analysis of these results can be performed, e.g., by Schild analysis. See Arunlakshana and Schild (1959) *Br. J. of Pharmacol.* 14:48–58; and Chapter 9 of Kenakin (1987) *Pharmacological Analysis of Drug-Receptor Interaction* Raven Press, N.Y. See also Black (1989) *Science* 245:486–493. Schild analysis with a defined antagonist provides a number of means to evaluate quantity and quality of both agonist and receptor preparations. For example, analysis of a preparation of agonist allows better quality control indications than ELISA or mere bioassay quantitation methods. It provides means to distinguish between a denatured agonist, which is more likely to test positive in ELISA assays, and a biologically active agonist.

The described muteins are typically proteinaceous, though a full length is not necessary. Fragments can be useful where they include positions which have been mutated as provided herein.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids. Virtually full length molecules with few substitutions will be preferred in most circumstances.

Substantially pure typically means that the mutein is free from other contaminating proteins, nucleic acids, and other biologicals derived from the original source organism. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS or CHAPS, or a low enough concentration as to avoid significant disruption of structural or physiological properties of the ligand.

III. Physical Variants

This invention also encompasses proteins or peptides having sequence variations at positions corresponding to the specified residues, but with substantial amino acid sequence identity at other segments. The variants include species variants and particularly molecules with the same primary sequence but variations beyond primary amino acid sequence, e.g., glycosylation or other modifications.

Amino acid sequence homology, or sequence identity, is determined by optimizing residue matches, if necessary, by introducing gaps as required. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group, Madison, Wis.;. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Members of a group do exhibit less dramatic structural differences, which may also be important. Substitutions at designated positions, e.g., at solvent exposed residues, can often be made with homologous residues to retain similar activities, e.g., agonist or antagonist functions. Identity measures will be at least about 85%, usually at least about 95%, preferably at least about 97%, and more preferably at least 98% or more, especially about the particular residue positions identified as appropriate for sequence changes. Regions of particular importance are within about 5 amino acids surrounding the defined positions, more particularly within about 8 amino acids, and preferably within about 11 amino acids adjacent the positions where changes are indicated.

The isolated cytokine DNA can be readily modified by nucleotide substitutions, nucleotide deletions, nucleotide insertions, and inversions of nucleotide stretches. These modifications result in novel DNA sequences which encode these proteins having many similar physiological, immunogenic, antigenic, or other functional activity. Enhanced expression may involve gene amplification, increased transcription, increased translation, and other mechanisms.

Cytokine mutagenesis can also be conducted by making amino acid insertions or deletions. Substitutions, deletions, insertions, or any combinations may be generated to arrive at a final construct. Insertions include amino-or carboxy—terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook, et al. (1989); Ausubel, et al. (1987 and Supplements); and Kunkel, et al. (1987) *Meth. Enzymol.* 154:367–382.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences.

In addition, new constructs may be made from combining similar functional domains from other proteins. For example, ligand-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

"Derivatives" of these cytokines include amino acid sequence mutants at other positions remote from those specified, glycosylation variants, and covalent or aggregate conjugates with other chemical moieties. Covalent derivatives can be prepared by linkage of functionalities to groups which are found in amino acid side chains or at the N- or C-termini, by standard means. See, e.g., Lundblad and Noyes (1988) *Chemical Reagents for Protein Modification*, vols. 1–2, CRC Press, Inc., Boca Raton, Fla.; Hugli (ed.) (1989) *Techniques in Protein Chemistry*, Academic Press, San Diego, Calif.; and Wong (1991) *Chemistry of Protein Conjugation and Cross Linking*, CRC Press, Boca Raton, Fla.

In particular, glycosylation alterations are included, e.g., made by modifying the glycosylation patterns of a polypeptide during its synthesis and processing, or in further processing steps. See, e.g., Elbein (1987) *Ann. Rev. Biochem.* 56:497–534. Also embraced are versions of the peptides with the same primary amino acid sequence which have other minor modifications, including phosphorylated amino acid residues, e.g., phosphotyrosine, phosphoserine, or phosphothreonine.

Fusion polypeptides between these cytokine muteins and other homologous or heterologous proteins are also provided. Many growth factors and cytokines are homodimeric entities, and a repeat construct may have various advantages, including lessened susceptibility to proteolytic cleavage. Typical examples are fusions of a reporter polypeptide, e.g., luciferase, with a segment or domain of a ligand, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1–3, Cold Spring Harbor Laboratory; and Ausubel, et al. (eds.) (1993) *Current Protocols in Molecular Biology*, Greene and Wiley, N.Y. Techniques for synthesis of polypeptides are described, e.g., in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach*, IRL Press, Oxford; and Grant (1992) *Synthetic Peptides: A User's Guide*, W. H. Freeman, N.Y.

This invention also contemplates the use of derivatives of these Ob muteins other than variations in amino acid sequence or glycosylation. Such derivatives may involve covalent or aggregative association with chemical moieties. Covalent or aggregative derivatives will be useful as immunogens, as reagents in immunoassays, or in purification methods such as for affinity purification of receptors or other binding ligands. An Ob mutein can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-cytokine antibodies or its receptor. The Ob muteins can also be labeled with a detectable group, for use in diagnostic assays. Purification of Ob muteins may be effected by immobilized antibodies or receptor.

The present invention contemplates corresponding muteins the isolation of additional closely related species variants, e.g., rodents, lagomorphs, carnivores, artiodactyla, perissodactyla, and primates.

The invention also provides means to isolate a group of related muteins displaying both distinctness and similarities in structure, expression, and function. Elucidation of many of the physiological effects of the muteins will be greatly accelerated by the isolation and characterization of distinct species variants.

The isolated genes encoding muteins will allow transformation of cells lacking expression of a corresponding Ob protein, e.g., either species types or cells which exhibit negative background activity.

Dissection of critical structural elements which effect the various receptor mediated functions provided by cytokine binding is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390.

IV. Nucleic Acids

The described peptide sequences are readily made by expressing a DNA clone encoding the mutein, e.g., modified from a natural source, or a synthetic gene. The synthetic gene may be based upon a preferred codon usage, e.g., for production in bacteria. A number of different approaches should be available to successfully produce a suitable nucleic acid clone.

The purified protein or defined peptides are useful as described above. Synthetic peptides or purified protein can be presented to an immune system to generate monoclonal or polyclonal antibodies which recognize specifically the muteins. See, e.g., Coligan (1991) *Current Protocols in Immunology* Wiley/Greene; and Harlow and Lane (1989) *Antibodies: A Laboratory Manual*, Cold Spring Harbor Press.

This invention contemplates use of isolated DNA or fragments to encode a biologically active corresponding mutein. In addition, this invention covers isolated or recombinant DNA which encodes a biologically active antagonist or partial agonist protein or polypeptide.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, marker or purification tags, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides.

Recombinant clones derived from genomic sequences, e.g., containing introit, will be useful for transgenic studies, including, e.g., transgenic cells and organisms, and for gene therapy. See, e.g., Goodnow (1992) "Transgenic Animals" in Roitt (ed.) *Encyclopedia of Immunology*, Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987) (ed.) *Teratocarcinomas and Embryonic Stem Cells: A Practical Approach*, IRL Press, Oxford; and Rosenberg (1992) *J. Clinical Oncology* 10:180–199.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence encoding a mutein.

V. Antibodies

Antibodies can be raised to portions of Ob proteins and which bind to the muteins described herein, including species or allelic variants, and fragments thereof. Additionally, antibodies can be raised to Ob muteins in either their active forms or in their inactive forms. Anti-idiotypic antibodies are also contemplated.

Antibodies, including binding fragments and single chain versions, against predetermined fragments of the ligands can be raised by immunization of animals with conjugates of fragments with immunogenic proteins. Monoclonal antibodies are prepared from cells secreting the desired antibody. These antibodies can be screened for binding to fragments containing sequences including the specified modifications. These monoclonal antibodies will usually bind with at least a $K_D$ of about 1 mM, more usually at least about 300 $\mu$M, typically at least about 100 $\mu$M, more typically at least about 30 $\mu$M, preferably at least about 10 $\mu$M, and more preferably at least about 3 $\mu$M or better.

The antibodies of this invention can also be useful in diagnostic applications. See e.g., Chan (ed.) (1987) *Immunology: A Practical Guide*, Academic Press, Orlando, Fla.; Price and Newman (eds.) (1991) *Principles and Practice of Immunoassay*, Stockton Press, N.Y.; and Ngo (ed.) (1988) *Nonisotopic Immunoassay*, Plenum Press, N.Y.

Mutein fragments may be joined to other materials, particularly polypeptides, as fused or covalently joined polypeptides to be used as immunogens. A mutein or its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; Williams, et al. (1967) *Methods in Immunology and Immunochemistry*, vol. 1, Academic Press, N.Y.; and Harlow and Lane (1988) *Antibodies: A Laboratory Manual*, CSH Press, N.Y., for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.), Academic Press, N.Y.; and particularly in Kohler and Milstein (1975) in *Nature* 256:495–497, which discusses one method of generating monoclonal antibodies. Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; Moore, et al., U.S. Pat. No. 4,642,334; and Queen, et al. (1989) *Proc. Nat'l Acad. Sci. USA* 86:10029–10033.

The antibodies of this invention can also be used for affinity chromatography in isolating the Ob proteins. Columns can be prepared where the antibodies are linked to a solid support. See, e.g., Wilchek et al. (1984) *Meth. Enzymol.* 104:3–55.

Antibodies raised against each mutein will also be useful to raise anti-idiotypic antibodies. These will be useful in detecting or diagnosing various immunological conditions related to expression of the respective antigens.

VI. Making Agonists and Antagonists

DNA which encodes the Ob proteins or fragments thereof can be obtained by chemical synthesis, screening cDNA libraries, or screening genomic libraries prepared from a wide variety of cell lines or tissue samples. See, e.g., Okayama and Berg (1982) *Mol. Cell. Biol.* 2:161–170; Gubler and Hoffman (1983) *Gene* 25:263–269; and Glover (ed.) (1984) *DNA Cloning: A Practical Approach*, IRL Press, Oxford. Suitable sequences can be obtained from GenBank.

This DNA can be mutated for expression in a wide variety of host cells for the synthesis of a full-length mutein or fragments which can in turn, e.g., be used to generate polyclonal or monoclonal antibodies; for binding studies; for construction and expression of modified molecules; and for structure/function studies.

Vectors, as used herein, comprise plasmids, viruses, bacteriophage, integratable DNA fragments, and other vehicles which enable the integration of DNA fragments into the genome of the host. See, e.g., Pouwels, et al. (1985 and Supplements) *Cloning Vectors: A Laboratory Manual*, Elsevier, N.Y.; Rodriguez, et al. (1988) (eds.) *Vectors: A Survey of Molecular Cloning Vectors and Their Uses*, Buttersworth, Boston, Mass.;

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See e.g., Rodriguez, et al., Chapter 10, pp. 205–236; Balbas and Bolivar (1990) *Methods in Enzymology* 185:14–37; and Ausubel, et al. (1993) *Current Protocols in Molecular Biology*, Greene and Wiley, N.Y.

Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610, see, e.g., Miller (1988) *Ann. Rev. Microbiol.* 42:177–199.

It will often be desired to express a mutein or polypeptide in a system which provides a specific or defined glycosylation pattern. See, e.g., Luckow and Summers (1988) *Bio/Technology* 6:47–55; and Kaufman (1990) *Meth. Enzymol.* 185:487–511.

The appropriate mutein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Once a particular mutein has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York; Villafranca (ed.) (1991) *Techniques in Protein Chemistry II*, Academic Press, San Diego, Calif.; and Coligan, et al. (es.) (1996 and periodic supplements) *Current Protocols in Protein Science* John Wiley and Sons, Inc., New York, N.Y. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes. See also chemical ligation, e.g., Dawson, et al. (1994) *Science* 266:776–779, a method of linking long synthetic peptides by a peptide bond.

VII. Uses

The present invention provides reagents which will find use in therapeutic or diagnostic applications as described elsewhere herein, e.g., in the general description for developmental abnormalities, or below in the description of kits for diagnosis.

The Ob protein muteins, fragments thereof, and antibodies thereto, should be useful in the evaluation or quality control of recombinant production of natural Ob. They may also be useful in vitro or in vivo screening or treatment of conditions associated with abnormal physiology or development, including abnormal proliferation, e.g., cancerous conditions, or degenerative conditions. The structural relationship of the Ob protein to other cytokines suggests the possibility of biological activities beyond the food metabolic activities described. In particular, modulation of cytokine activities should be useful in situations where the cytokine functions have been implicated, e.g., immunological responses, inflammation, autoimmunity, abnormal proliferation, regeneration, degeneration, and atrophy of responsive cell types. For example, a disease or disorder associated with abnormal expression or abnormal signaling by Ob protein, besides the recognized effects, should be a potential target for treatment using an antagonist or agonist. The similarity in structures and mechanisms suggest potential hematopoietic or immunological functions may also exist.

Recombinant Ob protein muteins or, in some instances, antibodies can be purified and then administered to a patient. These reagents can be combined for therapeutic use with additional active or inert ingredients, e.g., in conventional pharmaceutically acceptable carriers or diluents, e.g., appetite suppressors, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration. See, e.g., Langer (1990) *Science* 249:1527–1533.

These Ob protein muteins may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds.) (1993) *Pharmaceutical Dosage Forms: Parenteral Medications*, Dekker, N.Y.; Lieberman, et al. (eds.) (1990) *Pharmaceutical Dosage Forms: Tablets*, Dekker, N.Y.; and Lieberman, et al. (eds.) (1990) *Pharmaceutical Dosage Forms: Disperse Systems*, Dekker, N.Y. The therapy of this invention may be combined with or used in association with other agents.

The muteins of this invention are particularly useful in kits and assay methods which are capable of screening compounds for interactions with binding proteins. Two such binding proteins have sequences disclosed in SEQ ID NO: 4 and 5. These proteins each bind to Ob with specificity and high affinity. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate.

For example, antagonists can normally be found once the ligand has been structurally defined. Testing of potential ligand analogs is now possible, based upon an in vivo activity assay, or upon binding protein interaction. In particular, new agonists and antagonists will be discovered by using screening techniques described herein.

One method of drug screening utilizes eukaryotic or prokaryotic host cells which are stably transformed with recombinant DNA molecules expressing the binding protein. Cells may be isolated which express a binding protein in isolation from any others. Such cells, either in viable or fixed form, can be used for standard ligand/receptor binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses.

Rational drug design may also be based upon structural studies of the molecular shapes of the agonists or antagonists and other effectors or analogs. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, N.Y.

VIII. Kits

This invention also contemplates use of these muteins, proteins, fragments thereof, peptides, and their fusion products in a variety of diagnostic kits and methods for diagnosing the receptor interactions of a cytokine. Typically the kit will have a compartment containing either a defined mutein peptide or a reagent which recognizes one, e.g., receptor fragments or antibodies.

A kit for determining the binding affinity of a test compound to a binding protein or receptor would typically comprise a test compound; a labeled compound, for example a receptor or antibody having known binding affinity for the cytokine or its mutein; a source of mutein; and a means for separating bound from free labeled compound, such as a solid phase for immobilizing the mutein. Once compounds are screened, those having suitable binding affinity can be evaluated in suitable biological assays, as are well known in the art, to determine whether they act as agonists or antagonists.

Antibodies, including antigen binding fragments, specific for muteins or unique fragments are useful in diagnostic applications to detect the presence of the muteins. In certain circumstances, it will be useful to quantitate amounts of muteins in a sample. Diagnostic assays may be homogeneous (without a separation step between free reagent and antigen-ligand complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol.* 70:1–525; Harlow and Lane (1980) *Antibodies: A Laboratory Manual*, CSH Press, N.Y.; and Coligan, et al. (eds.) (1993) *Current Protocols in Immunology*, Greene and Wiley, N.Y.

Anti-idiotypic antibodies may have similar use to diagnose presence of antibodies against a mutein, as such may be diagnostic of various abnormal states.

Frequently, the reagents for diagnostic assays are supplied in kits, so as to optimize the sensitivity of the assay. For the subject invention, depending upon the nature of the assay, the protocol, and the label, either labeled or unlabeled antibody or receptor, or labeled mutein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In many of these assays, the test compound, mutein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free ligand, or alternatively the bound from the free test compound. The mutein can be immobilized on various matrixes followed by washing. Suitable matrixes include plastic such as an ELISA plate, filters, and beads. See, e.g., Coligan, et al. (eds.) (1993) *Current Protocols in Immunology*, Vol. 1, Chapter 2, Greene and Wiley, N.Y. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

All references cited herein are incorporated herein by reference to the same extent as if each individual publication or patent application was specifically and individually indicated to be incorporated by reference.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning. A Laboratory Manual*, Cold Spring Harbor Laboratory, Cold Spring Harbor Press; Sambrook, et al. (1989) *Molecular Cloning: A Laboratory Manual* (2d ed.), vols. 1–3, CSH Press, N.Y.; Ausubel, et al., *Biology*, Greene Publishing Associates, Brooklyn, N.Y.; Ausubel, et al. (1987 and Supplements) *Current Protocols in Molecular Biology*, Greene and Wiley, N.Y.; Innis, et al. (eds.) (1990) *PCR Protocols: A Guide to Methods and Applications*, Academic Press, N.Y.; or Coligan, et al. (es.) (1996 and periodic supplements) *Current Protocols in Protein Science* John Wiley and Sons, Inc., New York, N.Y. Methods for protein purification include such methods as ammonium sulfate precipitation, column chromatography, electrophoresis, centrifugation, crystallization, and others. See, e.g, Ausubel, et al. (1987 and periodic supplements); Deutscher (1990) "Guide to Protein Purification" in *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering Principle and Methods* 12:87–98, Plenum Press, N.Y.; Crowe, et al. (1992) *OIAexpress: The High Level Expression & Protein Purification System* QIAGEN, Inc., Chatsworth, Calif.; and Coligan, et al. (es.) (1996 and periodic supplements) *Current Protocols in Protein Science* John Wiley and Sons, Inc., New York, N.Y. Cell culture techniques are described in Doyle, et al. (eds.) (1994) *Cell and Tissue Culture: Laboratory Procedures*, John Wiley and Sons, NY.

FACS analyses are described in Melamed, et al. (1990) *Flow Cytometry and Sorting* Wiley-Liss, Inc., New York, N.Y.; Shapiro (1988) *Practical Flow Cytometry Liss*, New York, N.Y.; and Robinson, et al. (1993) *Handbook of Flow Cytometry Methods* Wiley-Liss, New York, N.Y.

II. Modifications to Ob Protein Sequence

Methods for expression of a mutein Ob protein are as applied to a cytokine in E. coli described, e.g., in Zurawski, et al. (1986) *J. Immunol* 137:3354–3360; Zurawski and Zurawski, et al. (1988) *EMBO J.* 7:1061–1069; and Coligan, et al. (eds.) (1996 and periodic supplements) *Current Protocols in Protein Science* John Wiley and Sons, Inc., New York, N.Y. Cassette substitution mutagenesis is described in Zurawski and Zurawski (1989) *EMBO J.* 8:2583–2590. For instance, a synthetic gene may be constructed by linking synthetic oligonucleotides, the gene sequence selected from preferred codon usage in, e.g., E. coli. In addition, a purification sequence, e.g., a FLAG signal may be added to assist in purification and/or detection. Refolding of recombinant protein may be performed using standard methods.

III. Biological Assay of Sequence Variants

Biological assay of Ob is described, e.g., in Pelleymounter, et al. (1995) *Science* 269:540–543; Halaas, et al. (1995) *Science* 269:543–546; and Campfield, et al. (1995) *Science* 269:546–548. Binding of the variants to the receptor may be assayed by standard binding assays, including surface plasmon resonance (BIAcore, Pharmacia) analysis. See Tartaglia, et al. (1995) *Cell* 83:1263–1271.

Alternatively, male ob/ob mice, aged 7 weeks, were individually housed in Nalgene metabolic cages in a reverse light (12 hours dark, 12 light) cycle room. Mice were given rodent chow pellets ad libitum. Mice were injected intraperitoneally (i.p.) with saline or 15 μg (in 0.18 ml; dilutions were done in sterile PBS) wild type or mutein, two times a day (b.i.d.) for three days. Injections occurred at onset of dark part of the cycle and 6 hours into the dark cycle. Food intake measurements were made at 2, 4, 6, and 24 hours post-first injection of each day. Body weight was measured each day prior to first injection of the day. Water intake, urine, and fecal output were also measured. Various means to measure metabolic rate are known in the art.

IV. Specific Variants

One variant corresponding to human K11E; K15E (in the A helix) exhibited about 50% activity of natural human Ob. A variant corresponding to a human Ob with deletion of the extruded loop exhibited virtually no biological activity, but maintained the ability to bind the Ob receptor. Other variants in the D helix corresponding to a human Ob R128E, D135K, R128E; D135K, and Q130K; Q134K showed biological activity equivalent to natural Ob.

These variations were selected primarily for the following reasons:

1. Ob is a member of the family of hematopoietic cytokines. There is much experimental data, e.g., from the interaction of growth hormone to its receptor, that the A and D helices are the primary ligand-receptor contact points, with a lesser effect from the C helix.
2. Residues in the A and D helices are selected that are exposed, and thus would contribute to receptor binding. Residues that make up the core of the helix bundle and are involved in general tertiary folding, are avoided. Note that certain of these residues point inside the helix and interact with one another to produce the helix, these are distinct from those which point outwards and would be solvent exposed.
3. For maximum effect, variations are selected that are as 'profound' as possible (e.g., when possible, charge reversal, R/K for E/D etc.).

These analyses have identified that there are at least two clearly exposed residues in the A-helix: K11 and K15. The double charge reversal variant shows an altered CD profile, suggesting that it is misfolded and which likely is the cause of the effects its biological activity. Its biological activity is reduced.

These analyses have also identified four exposed residues in helix-D. The Q130/Q134 residues are located in a position predicted to cause only a minor effect on receptor binding (based on other cytokine/receptor interactions). Experimental evidence confirms this, The Q130/Q134 variant is biologically as active as wild type Ob.

The other two exposed residues, R128 and D135 are much more likely to be involved in ligand-receptor interaction. CD analysis shows relatively unaltered tertiary structures for R128E, D135K and the double mutant R128E/D135K. Biological analysis shows R128E/D135K to be inactive, D135K is almost inactive and, surprisingly, R128E is inactive and possibly even 'less' than inactive. Mice injected with R128E eat even less than mice injected with saline.

Binding studies show that all three mutant proteins can still bind with the same affinity to the leptin receptor. This suggests that these two residues are directly contacting a second receptor in a complex that consists, at a minimum, of Ob, the Ob receptor, and another unidentified receptor component. These proteins should behave as antagonists.

Other variants include a loop deletion. In this Ob model, there is an unstructured loop of 9 residues following the C-helix and going into the long C/D loop. This region is unique, as no other helical cytokine has an equivalent region. A variant has been constructed which has deleted this region and its biological activity and biophysical behavior have been tested. There is a slight loss of alpha helicity, but the protein essentially is still biologically active. This is unexpected since this variant has a 9 amino acid deletion in the middle of the protein, but without affecting the protein fold. This provides strong evidence that the predicted fold for Ob and the positioning of this loop is correct.

V. Binding Protein Analysis

Binding analyses of Ob variants to an Ob binding protein can be performed, see SEQ ID NO: 4 or 5. Receptor is made by standard recombinant methods, expressing a gene encoding said proteins. Assays will include a heterologous displacement format with labeled ligand at an appropriate concentration and various concentrations of purified Ob or mutant Ob proteins. Ob proteins and variants can be purified, or used in crude preparations. Data can be analyzed using the Ligand computer program, see Munson and Rodbard (1980) *Anal. Biochem.* 107:220–239. Binding protein interaction analyses can also performed on L cells expressing an Ob binding protein or receptor, derived by cotransfection by expression plasmids.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated or recombinant mutein of a mammalian Ob which comprises:
   a) an amino acid sequence that differs from SEQ ID NO: 1 by a non-conservative amino acid residue substitution, wherein said substitution is at a position selected from the following group:
      D29, D30, K32, T33, K36, T37, V39, T40, I42, N43, N99, D100, E102, N103, R105, D106, and L107;
   b) an amino acid sequence that differs from SEQ ID NO:2 by a non-conservative amino acid residue substitution, wherein said substitution is at a position selected from the following group:
      D29, D30, K32, T33, K36, T37, V39, T40, I42, N43, N99, D100, E102, N103, R105, D106, and L107; or
   c) an amino acid sequence that differs from SEQ ID NO:3 by a non-conservative amino acid residue substitution, wherein said substitution is at a position selected from the following group:
      D29, D30, K32, T33, K36, T37, V39, T40, I42, N43, N99, D100, E102, N103, R105, D106, and L107.

2. The mutein of claim 1, wherein said substitution is selected from the group consisting of D29K, D30K, K32E, T33E, K36E, T37E, T40E, E102K, N103D, R105E, and D106K.

3. A composition comprising a mutein of claim 1 in a pharmaceutically acceptable carrier.

4. The mutein of claim 1, wherein said SEQ ID NO: is 1.

5. The mutein of claim 1, wherein said SEQ ID NO: is 2 or 3.

6. The mutein of claim 1, comprising an amino acid sequence that differs from SEQ ID NO:1 by a non-conservative amino acid residue substitution, wherein substitution is at a position selected from the group consisting of D29, D30, K32, T33, K36, T37, V39, T40, I42, and N43.

7. The mutein of claim 6, wherein the substitution is at position K32, T33, K36, T37, or T40.

8. The mutein of claim 7, wherein the substitution is at position K32 or K36.

9. The mutein of claim 1, comprising an amino acid sequence that differs from SEQ ID NO:1 by a non-conservative amino acid residue substitution, wherein said substitution is at a position selected from the group consisting of N99, D100, E102, N103, R105, D106, and L107.

10. The mutein of claim 9, wherein the substitution is at position E102, N103, R105, or D106.

11. A substantially pure or recombinant mutein of a mammalian Ob which comprises:
    a) an amino acid sequence that differs from SEQ ID NO:1 by an amino acid residue substitution, wherein said substitution is at a residue selected from residues 143–156 or 158 and is not substituted by Lys, Glu, Cys, or Pro;
    b) an amino acid sequence that differs from SEQ ID NO:2 by an amino acid residue substitution, wherein said substitution is at a residue selected from residues 143–156 or 158 and is not substituted by Lys, Glu, Cys, or Pro; or
    c) an amino acid sequence that differs from SEQ ID NO:3 by an amino acid residue substitution, wherein said substitution is at a residue selected from residues 143–156 or 158 and is not substituted by Lys, Glu, Cys, or Pro.

12. The mutein of claim 11, wherein said SEQ ID NO: is 1.

13. The mutein of claim 11, wherein said SEQ ID NO: is 2 or 3.

14. The mutein of claim 12, wherein said substitution is a non-conservative substitution.

15. The mutein of claim 13, wherein said substitution is a non-conservative substitution.

16. A composition comprising a mutein of claim 12 in a pharmaceutically acceptable carrier.

17. A composition comprising a mutein of claim 14 in a pharmaceutically acceptable carrier.

* * * * *